(12) United States Patent
Gunaratnam et al.

(10) Patent No.: US 9,808,589 B2
(45) Date of Patent: Nov. 7, 2017

(54) METHOD FOR ASSEMBLING A PATIENT INTERFACE

(71) Applicant: ResMed Limited, Bella Vista, New South Wales (AU)

(72) Inventors: Michael K Gunaratnam, Sydney (AU); Gregory S Smart, Sydney (AU); Philip R Kwok, Sydney (AU)

(73) Assignee: RESMED LIMITED, Bella Vista (AU)

( * ) Notice: Subject to any disclaimer, the term of this patent is extended or adjusted under 35 U.S.C. 154(b) by 574 days.

(21) Appl. No.: 14/176,402

(22) Filed: Feb. 10, 2014

(65) Prior Publication Data

US 2014/0150238 A1   Jun. 5, 2014

Related U.S. Application Data

(60) Continuation of application No. 12/314,975, filed on Dec. 19, 2008, now Pat. No. 8,667,965, which is a (Continued)

(30) Foreign Application Priority Data

Dec. 9, 1998  (AU) .................................. 3922/1998
Dec. 9, 1998  (AU) .................................. 3923-1998
(Continued)

(51) Int. Cl.
*A61M 16/06*  (2006.01)
*A61M 16/00*  (2006.01)
(Continued)

(52) U.S. Cl.
CPC ........ *A61M 16/0057* (2013.01); *A61M 16/06* (2013.01); *A61M 16/065* (2014.02);
(Continued)

(58) Field of Classification Search
CPC .......... A61M 16/0057; A61M 16/0638; A61M 16/0616; A61M 16/0633; A61M 16/06;
(Continued)

(56) References Cited

U.S. PATENT DOCUMENTS 35,724 A     6/1862   Wilcox
463,351 A   11/1891   Elliott
(Continued)

FOREIGN PATENT DOCUMENTS

CA           88122       11/1999
DE    297 21 766 U1      3/1998
(Continued)

OTHER PUBLICATIONS

Chen; David E.; U.S. Appl. No. 60/140,423; Jun. 22, 1999 (unpublished).*
(Continued)

*Primary Examiner* — Tan-Uyen (Jackie) T Ho
*Assistant Examiner* — Joseph D Boecker
(74) *Attorney, Agent, or Firm* — Nixon & Vanderhye, P.C.

(57) ABSTRACT

A respiratory mask assembly includes a rigid mask frame and a cushion. A clip secures the cushion to the frame.

25 Claims, 19 Drawing Sheets

Related U.S. Application Data continuation of application No. 11/297,410, filed on Dec. 9, 2005, now Pat. No. 7,487,777, which is a continuation of application No. 10/751,926, filed on Jan. 7, 2004, now Pat. No. 7,021,311, which is a division of application No. 10/123,484, filed on Apr. 17, 2002, now Pat. No. 6,796,308, which is a continuation of application No. 09/501,004, filed on Feb. 9, 2000, now Pat. No. 6,412,487, which is a continuation-in-part of application No. 09/498,705, filed on Feb. 7, 2000, now Pat. No. 6,491,034, and a continuation-in-part of application No. 09/316,227, filed on May 21, 1999, now Pat. No. 6,513,526, and a continuation-in-part of application No. 29/101,860, filed on Mar. 12, 1999, now Pat. No. Des. 428,139, and a continuation-in-part of application No. 29/101,861, filed on Mar. 12, 1999, now Pat. No. Des. 430,663, and a continuation-in-part of application No. 29/101,862, filed on Mar. 12, 1999, now Pat. No. Des. 428,988, and a continuation-in-part of application No. 29/115,618, filed on Dec. 16, 1999, now Pat. No. Des. 443,355.

(30) Foreign Application Priority Data

| | | |
|---|---|---|
| Dec. 9, 1998 | (AU) | 3924/1998 |
| Feb. 9, 1999 | (AU) | PP8550 |
| Jun. 18, 1999 | (AU) | 1916/99 |
| Jun. 18, 1999 | (AU) | PQ1029 |
| Jun. 18, 1999 | (AU) | PQ1040 |

(51) Int. Cl.
*A61M 16/08* (2006.01)
*A61M 16/20* (2006.01)

(52) U.S. Cl.
CPC .... *A61M 16/0616* (2014.02); *A61M 16/0622* (2014.02); *A61M 16/0633* (2014.02); *A61M 16/0638* (2014.02); *A61M 16/0666* (2013.01); *A61M 16/0683* (2013.01); *A61M 16/08* (2013.01); *A61M 16/208* (2013.01); *A61M 2210/0618* (2013.01); *Y10T 29/49863* (2015.01)

(58) Field of Classification Search
CPC .............. A61M 16/0683; A61M 16/08; A61M 16/0666; A61M 16/208; A61M 2210/0618; Y10T 29/49863; B63C 11/12; B63C 11/14; B63C 2011/128; A63B 33/00
USPC ........................... 128/206.24, 203.13, 207.12
See application file for complete search history.

(56) References Cited

U.S. PATENT DOCUMENTS

| | | |
|---|---|---|
| 715,611 A | 12/1902 | Schenker et al. |
| 716,530 A | 12/1902 | Giddens |
| 812,706 A | 2/1906 | Warbasse |
| 1,333,075 A | 3/1920 | Hill et al. |
| 1,381,826 A | 6/1921 | Hansen |
| 1,653,572 A * | 12/1927 | Jackson ............... A61M 16/06 128/203.13 |
| 1,672,165 A | 6/1928 | Lewis |
| 1,733,020 A | 10/1929 | Jones |
| 2,029,129 A | 1/1936 | Schwartz |
| 2,033,448 A | 3/1936 | James |
| 2,141,222 A | 12/1938 | Pioch |
| 2,359,506 A | 10/1944 | Battley et al. |
| 2,371,965 A | 3/1945 | Lehmberg |
| 2,454,103 A | 11/1948 | Swidersky |
| 2,638,161 A | 5/1953 | Jones |
| 2,823,671 A | 2/1958 | Garelick |
| 2,832,015 A | 4/1958 | Ortega |
| 2,893,387 A | 7/1959 | Gongoll et al. |
| 2,931,356 A | 4/1960 | Schwarz |
| 3,141,213 A | 7/1964 | Nicholas |
| 3,189,027 A | 6/1965 | Bartlett, Jr. |
| 3,413,972 A * | 12/1968 | Depping ............... A62B 18/045 128/201.23 |
| 3,474,783 A | 10/1969 | Ulmann |
| 3,494,072 A | 2/1970 | Olson |
| 3,523,534 A | 8/1970 | Nolan |
| 3,535,810 A | 10/1970 | Baehrle |
| 3,555,752 A | 1/1971 | Bogaert |
| 3,824,999 A * | 7/1974 | King ................ A61M 16/0465 128/207.17 |
| 4,049,357 A | 9/1977 | Hamisch, Jr. |
| 4,064,875 A | 12/1977 | Cramer et al. |
| 4,111,197 A | 9/1978 | Warncke et al. |
| 4,121,580 A | 10/1978 | Fabish |
| 4,164,942 A | 8/1979 | Beard et al. |
| 4,226,234 A | 10/1980 | Gunderson |
| 4,274,404 A | 6/1981 | Molzan et al. |
| 4,380,102 A | 4/1983 | Hansson |
| 4,494,538 A | 1/1985 | Ansite |
| 4,506,665 A | 3/1985 | Andrews et al. |
| 4,549,334 A | 10/1985 | Miller |
| 4,580,556 A | 4/1986 | Kondur |
| 4,606,340 A | 8/1986 | Ansite |
| 4,622,964 A | 11/1986 | Flynn |
| 4,633,972 A | 1/1987 | DeRocher |
| 4,783,029 A | 11/1988 | Geppert et al. |
| 4,794,921 A | 1/1989 | Lindkvist |
| 4,807,617 A * | 2/1989 | Nesti ................ A61M 16/0833 128/203.29 |
| 4,809,692 A | 3/1989 | Nowacki et al. |
| 4,835,820 A | 6/1989 | Robbins, III |
| 4,841,953 A | 6/1989 | Dodrill |
| 4,870,963 A | 10/1989 | Carter |
| 4,875,714 A | 10/1989 | Lee |
| 4,898,174 A | 2/1990 | Fangrow, Jr. |
| 4,899,614 A | 2/1990 | Kataumi |
| 4,974,586 A | 12/1990 | Wandel et al. |
| 4,981,134 A | 1/1991 | Courtney |
| 4,997,217 A | 3/1991 | Kunze |
| 5,003,633 A | 4/1991 | Itoh |
| 5,005,568 A | 4/1991 | Loescher et al. |
| 5,062,420 A | 11/1991 | Levine |
| 5,080,094 A | 1/1992 | Tayebi |
| 5,136,760 A | 8/1992 | Sano et al. |
| 5,215,336 A | 6/1993 | Worthing |
| 5,243,971 A * | 9/1993 | Sullivan ............... A61M 16/06 128/204.18 |
| 5,253,641 A | 10/1993 | Choate |
| 5,265,595 A * | 11/1993 | Rudolph ................ A61B 5/097 128/204.18 |
| 5,311,862 A | 5/1994 | Blasdell et al. |
| 5,398,673 A | 3/1995 | Lambert |
| 5,438,981 A | 8/1995 | Starr et al. |
| 5,501,214 A | 3/1996 | Sabo |
| 5,538,001 A | 7/1996 | Bridges |
| 5,645,049 A | 7/1997 | Foley et al. |
| 5,647,355 A | 7/1997 | Starr et al. |
| 5,647,357 A * | 7/1997 | Barnett ................ A61M 16/06 128/205.25 |
| 5,676,133 A | 10/1997 | Hickle et al. |
| 5,709,204 A | 1/1998 | Lester |
| 5,724,965 A * | 3/1998 | Handke ................ A61M 16/06 128/205.25 |
| 5,794,617 A | 8/1998 | Brunell et al. |
| 5,839,436 A | 11/1998 | Fangrow et al. |
| 5,860,677 A | 1/1999 | Martins et al. |
| 5,896,857 A | 4/1999 | Hely et al. |
| 5,909,732 A | 6/1999 | Diesel et al. |
| 5,918,598 A * | 7/1999 | Belfer ................ A41D 13/1176 128/205.25 |

(56) References Cited

U.S. PATENT DOCUMENTS

| | | |
|---|---|---|
| 5,921,239 A | 7/1999 | McCall et al. |
| 5,937,851 A | 8/1999 | Serowski et al. |
| 5,979,025 A | 11/1999 | Horng |
| 6,006,748 A | 12/1999 | Hollis |
| D428,139 S | 7/2000 | Smart |
| 6,082,360 A * | 7/2000 | Rudolph ............... A61M 16/06 128/206.24 |
| D428,988 S | 8/2000 | Smart |
| D430,663 S | 9/2000 | Smart |
| 6,119,693 A | 9/2000 | Kwok et al. |
| 6,161,538 A * | 12/2000 | Bonhomme ........... A62B 18/04 128/204.21 |
| 6,189,532 B1 | 2/2001 | Hely et al. |
| 6,192,886 B1 | 2/2001 | Rudolph |
| 6,196,223 B1 * | 3/2001 | Belfer ................ A41D 13/1176 128/205.25 |
| D443,355 S | 6/2001 | Gunaratnam et al. |
| 6,240,605 B1 | 6/2001 | Stevens et al. |
| 6,250,375 B1 | 6/2001 | Lee et al. |
| 6,256,846 B1 | 7/2001 | Lee |
| 6,272,722 B1 | 8/2001 | Lai |
| 6,321,421 B1 | 11/2001 | Lim |
| 6,381,813 B1 | 5/2002 | Lai |
| 6,397,847 B1 * | 6/2002 | Scarberry ............. A61M 16/06 128/206.14 |
| 6,412,487 B1 | 7/2002 | Gunaratnam et al. |
| 6,449,817 B1 | 9/2002 | Hsu |
| 6,463,931 B1 | 10/2002 | Kwok et al. |
| 6,491,034 B1 | 12/2002 | Gunaratnam et al. |
| 6,513,206 B1 | 2/2003 | Banitt et al. |
| 6,513,526 B2 | 2/2003 | Kwok et al. |
| 6,520,182 B1 | 2/2003 | Gunaratnam |
| 6,532,961 B1 | 3/2003 | Kwok et al. |
| 6,615,832 B1 * | 9/2003 | Chen ..................... A62B 18/08 128/205.25 |
| 6,631,718 B1 * | 10/2003 | Lovell ................... A61M 16/06 128/206.24 |
| 6,691,708 B2 | 2/2004 | Kwok et al. |
| 6,701,927 B2 | 3/2004 | Kwok et al. |
| 6,796,308 B2 | 9/2004 | Gunaratnam et al. |
| 7,021,311 B2 | 4/2006 | Gunaratnam et al. |
| 7,207,334 B2 | 4/2007 | Smart |
| 7,487,777 B2 | 2/2009 | Gunaratnam |
| 7,861,714 B2 | 1/2011 | Smart |
| 2002/0236450 | 11/2001 | Gunaratnam et al. |
| 2002/0023649 A1 | 2/2002 | Gunaratnam et al. |
| 2002/0129818 A1 * | 9/2002 | Morgan ................. A62B 18/08 128/206.26 |
| 2002/0153012 A1 | 10/2002 | Gunaratnam et al. |
| 2002/0174868 A1 | 11/2002 | Kwok et al. |
| 2003/0005935 A1 | 1/2003 | Kwok et al. |
| 2004/0134497 A1 | 7/2004 | Gunaratnam et al. |
| 2006/0130843 A1 | 6/2006 | Gunaratnam et al. |

FOREIGN PATENT DOCUMENTS

| | | |
|---|---|---|
| DE | 4 99 00 269.5 | 1/1999 |
| EP | 1 027 905 A3 | 8/2000 |
| ES | 145309 | 1/2000 |
| FR | 2 691 906 | 12/1993 |
| FR | 99/16 | 8/1999 |
| GB | 2080119 | 12/1998 |
| GB | 2080120 | 12/1998 |
| GB | 2080121 | 12/1998 |
| JP | 48-55696 | 10/1971 |
| JP | 59-55535 | 4/1984 |
| JP | 61-67747/86 | 5/1986 |
| JP | 7-21058/95 | 4/1995 |
| JP | 7-308381 | 11/1995 |
| JP | 9-501084 | 2/1997 |
| JP | 1105649 | 2/1999 |
| SE | 65481 | 8/2000 |
| WO | WO 80/01645 | 8/1980 |
| WO | WO 87/01950 | 4/1987 |
| WO | WO 95/04566 | 2/1995 |
| WO | WO 98/26830 | 6/1998 |
| WO | WO 98/48878 | 11/1998 |
| WO | WO 99/30760 | 6/1999 |
| WO | WO 00/38772 | 7/2000 |

OTHER PUBLICATIONS

Office Action mailed Nov. 22, 2012 in Canadian Application No. 2,733,839 (2 pages).
Office Action mailed Mar. 3, 2015 in U.S. Appl. No. 13/396,002 (12 pages).
Office Action mailed Oct. 24, 2014 in U.S. Appl. No. 13/396,002 (11 pages).
Office Action issued in U.S. Appl. No. 13/396,002, issued Oct. 8, 2013.
U.S. Patent Application No. 2012/0180794, filed on Feb. 14, 2012, Gregory Scott Smart.
ResMed, Mask Systems Product Brochure, 2 pages, Sep. 1992.
Respironics, Inc. "Nasal Mask System Silicone Contour Mask" Product Instructions, 2 pages, Jun. 1997.
Japanese Office Action English Translation for JP 2000-029094, 3 pages.
Respironics, Inc., "Nasal Mask System Silicone Contour Mask," Product Instructions, 2 pages, Jun. 1997.
The American Heritage Dictionary, Second College Edition, 1982, 3 pages.
Parent; U.S. Appl. No. 12/314,975, filed Dec. 19, 2008.
Extended European Search Report issued in related European Application No. EP 15192831.4 dated Oct. 6, 2016, 7 pages.

* cited by examiner

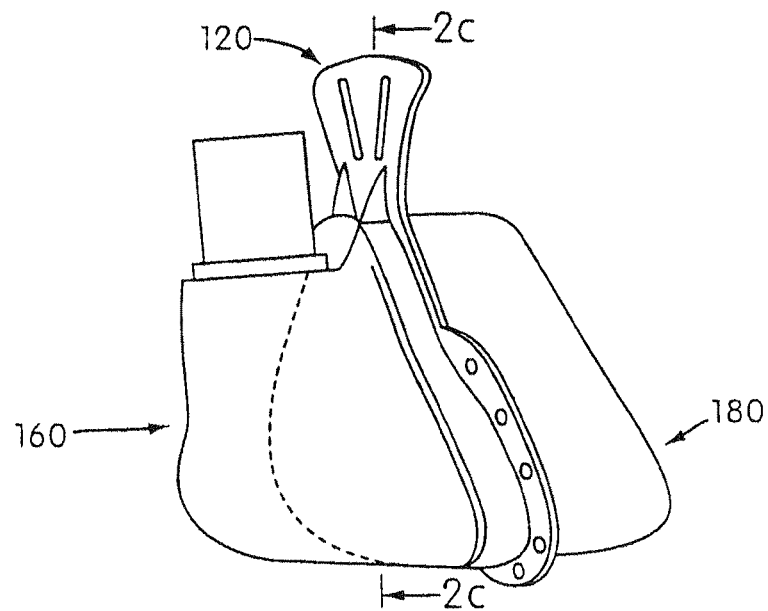
FIG. 2a
PRIOR ART
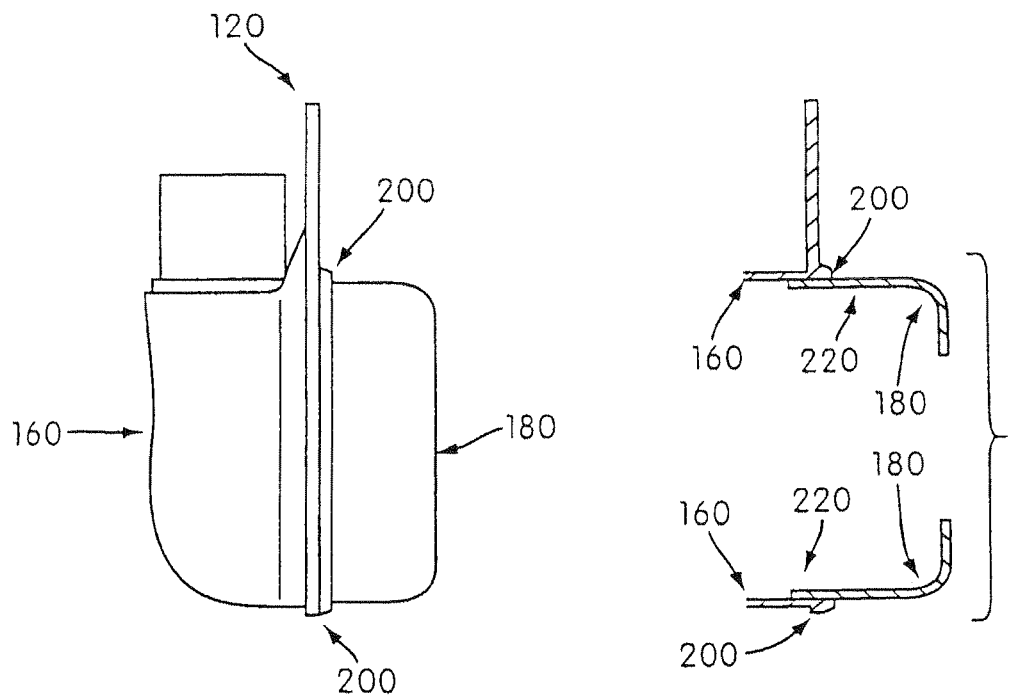
FIG. 2b
PRIOR ART
FIG. 2c
PRIOR ART

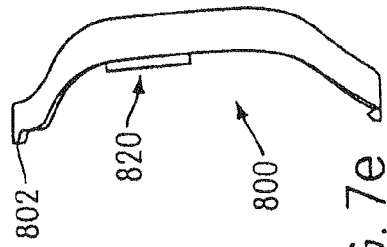
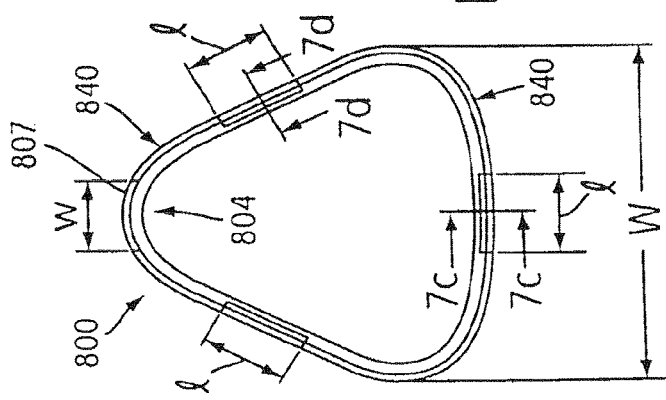
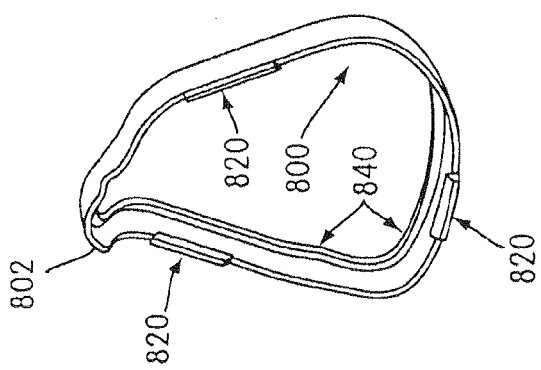
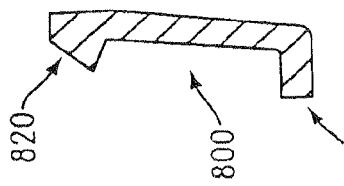

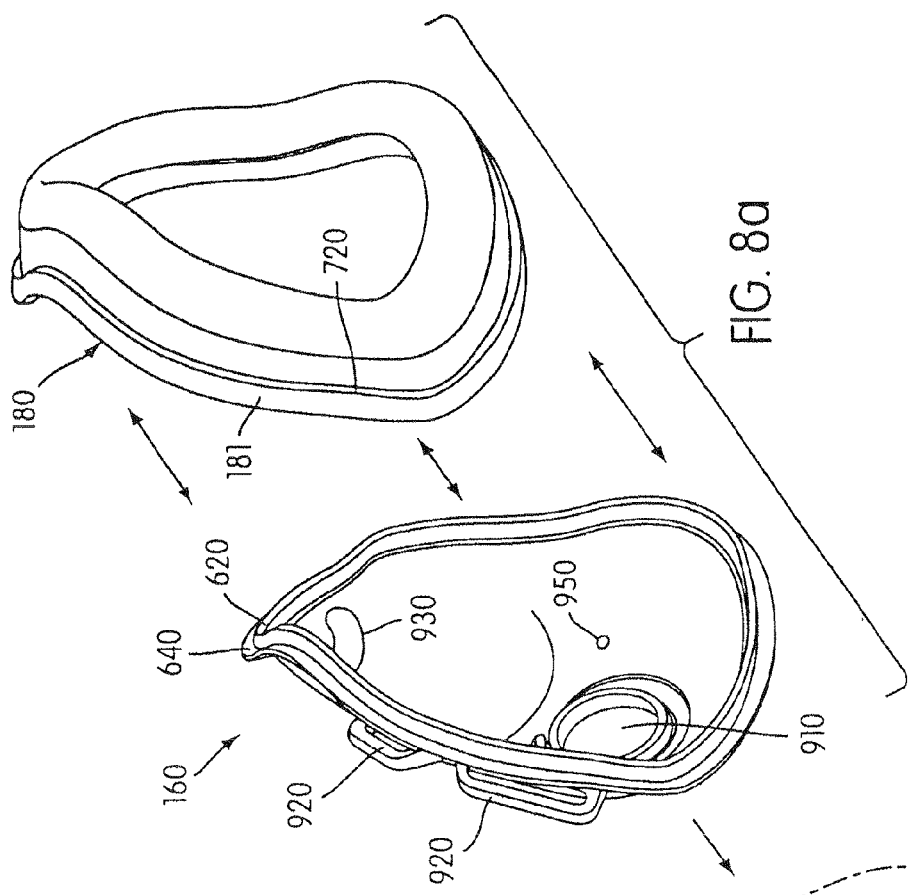
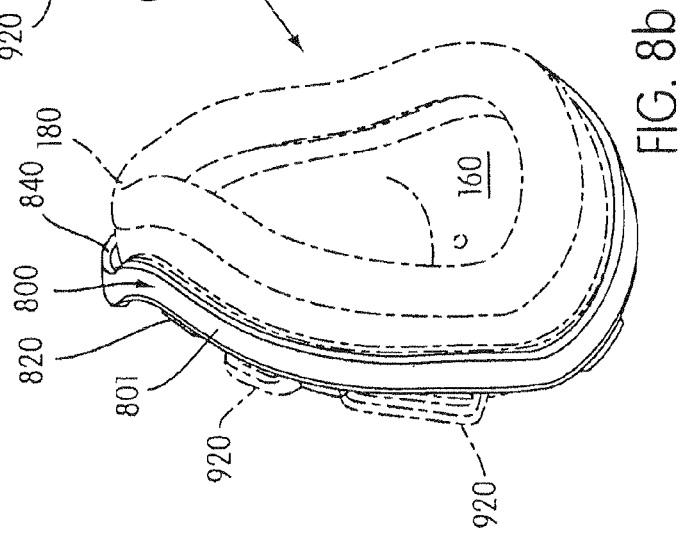
FIG. 8a
FIG. 8b

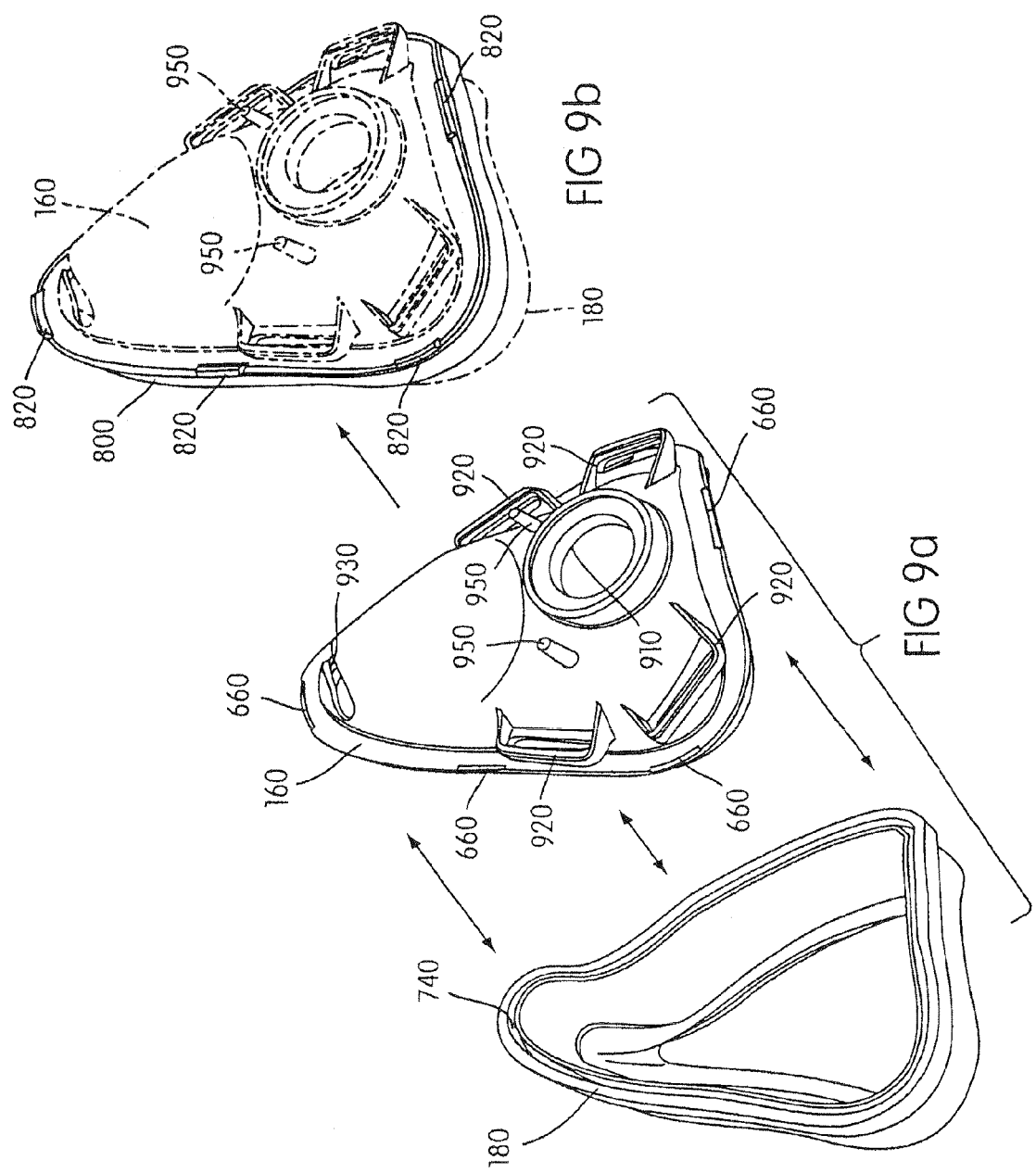

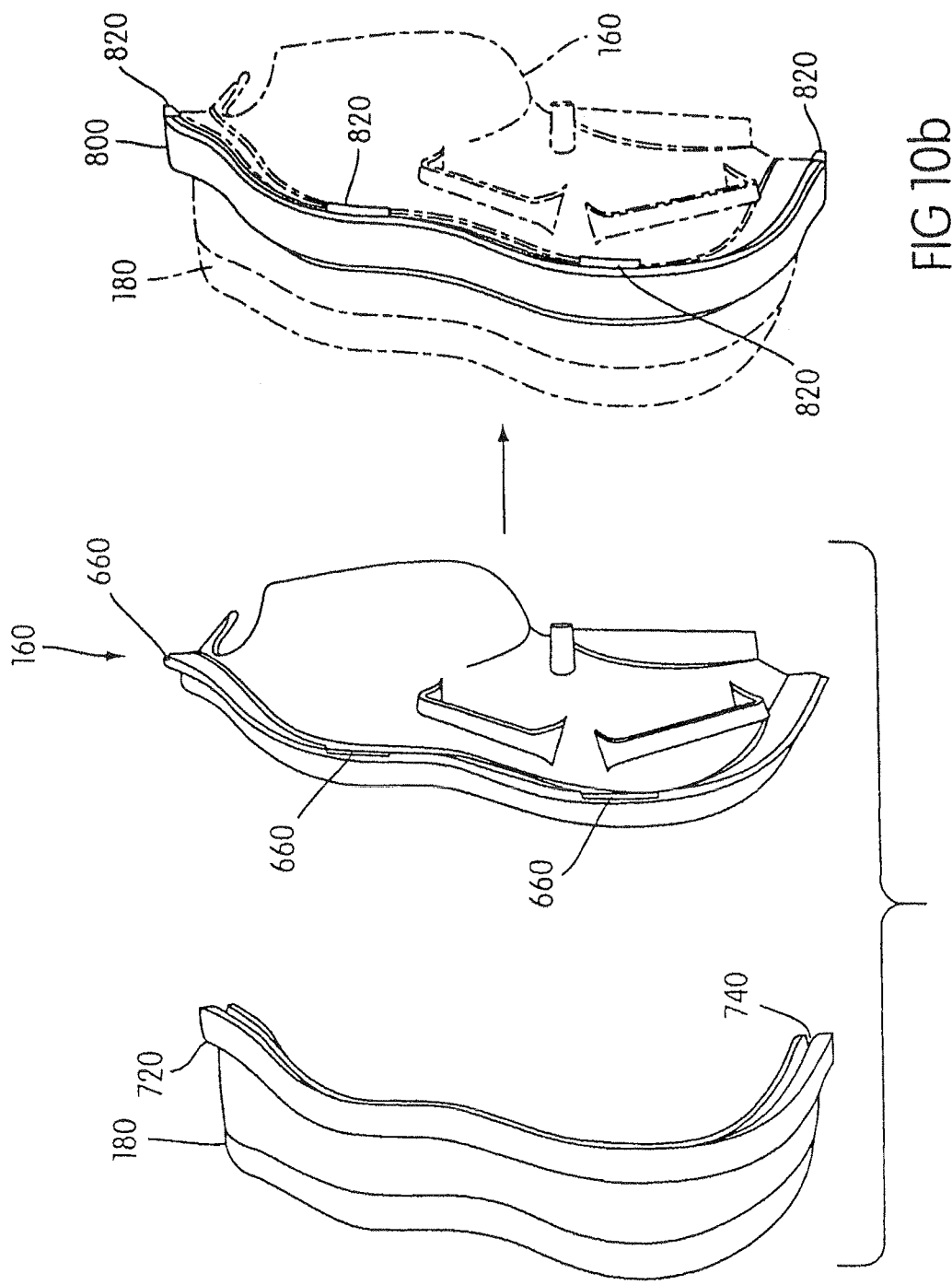

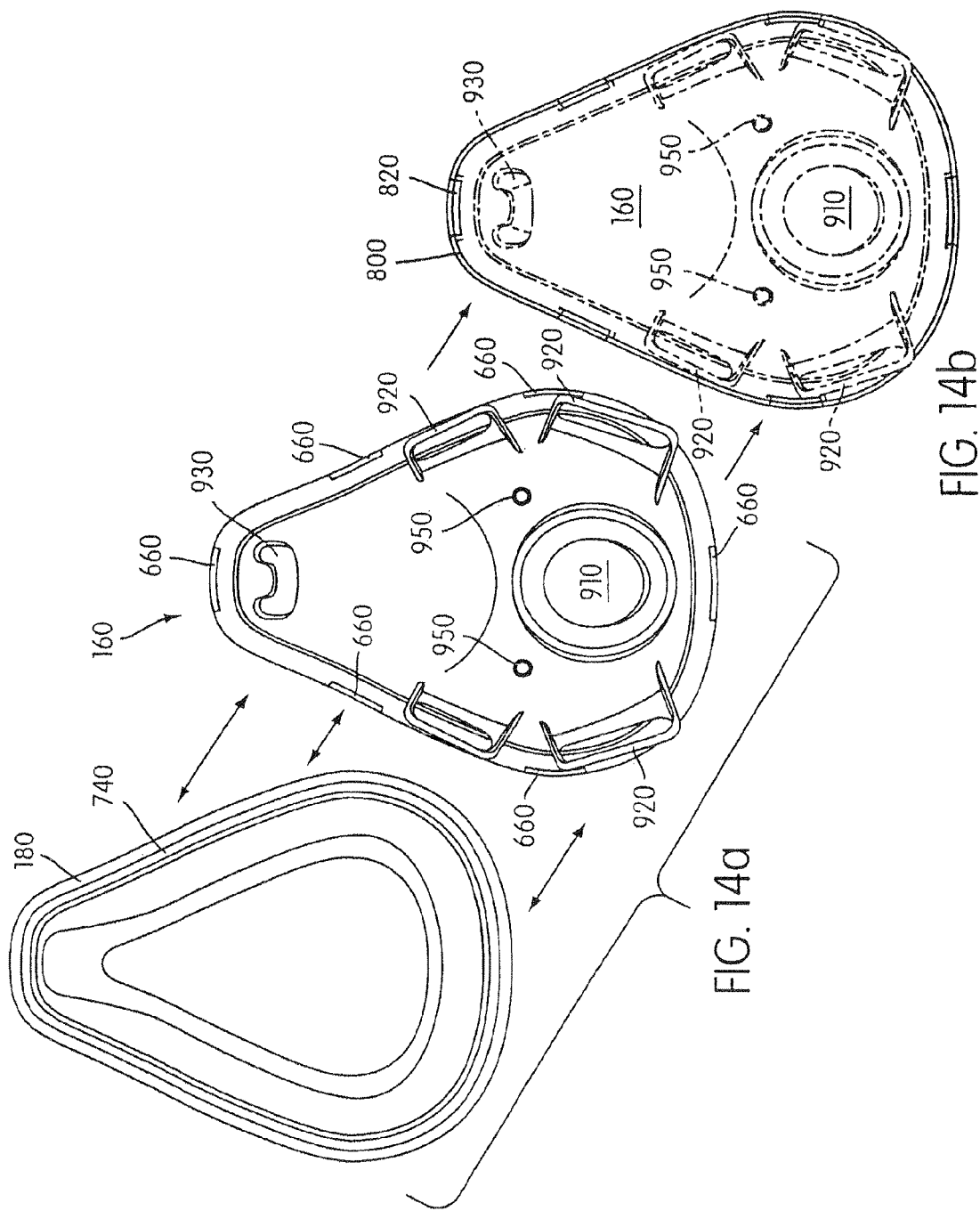

METHOD FOR ASSEMBLING A PATIENT INTERFACE

CROSS REFERENCE TO RELATED APPLICATIONS

This application is a Continuation of U.S. application Ser. No. 12/314,975, filed Dec. 19, 2008, now U.S. Pat. No. 8,667,965, which is a Continuation of U.S. application Ser. No. 11/297,410, filed Dec. 9, 2005, now U.S. Pat. No. 7,487,777, which is a Continuation of U.S. application Ser. No. 10/751,926, filed Jan. 7, 2004, now U.S. Pat. No. 7,021,311, which is a Divisional of U.S. application Ser. No. 10/123,484, filed Apr. 17, 2002, now U.S. Pat. No. 6,796,308, which is a Continuation of U.S. application Ser. No. 09/501,004, filed Feb. 9, 2000, now U.S. Pat. No. 6,412,487, which is a Continuation-in-Part (CIP) of U.S. application Ser. No. 09/498,705, filed Feb. 7, 2000, now U.S. Pat. No. 6,491,034, a CIP of U.S. application Ser. No. 09/316,227, filed May 21, 1999, now U.S. Pat. No. 6,513,526; a CIP of U.S. Design application No. 29/101,860, filed Mar. 12, 1999, now U.S. Design Pat. No. D428,139; a CIP of U.S. Design application No. 29/101,861, filed Mar. 12, 1999, now U.S. Design Pat. No. D430,663; a CIP of U.S. Design application No. 29/101,862, filed Mar. 12, 1999, now U.S. Design Pat. No. D428,988; and a CIP of U.S. Design application No. 29/115,618, filed Dec. 16, 1999, now U.S. Design Pat. No. D443,355, each of which is incorporated by reference in its entirety.

FIELD OF THE INVENTION

The invention relates to a method and apparatus for connecting a nasal or full-face mask cushion to a mask frame, where the mask is suitable for the delivery of breathable gases to a patient for the treatment of sleep disordered breathing (SDB).

BACKGROUND TO THE INVENTION

Nasal and full-face masks systems suitable for the delivery of air or other breathable gases to patients for the treatment of sleep disordered breathing may include a mask (100), a forehead support (120) and headgear (140), as depicted in FIG. 1. The mask may comprise a rigid shell (160), termed a frame, and a soft portion (180), termed a cushion. The frame may be constructed from a material such as polycarbonate, forming a cavity which overlies the patient's nose and/or mouth. The soft cushion may be constructed from a material such as silicone spacing the frame away from the patient's face to provide comfortable contact.

In the case of the Mirage® Mask (ResMed Limited), shown in FIG. 1, the headgear (140) is constructed from fabric and includes a rear portion which engages the region near the occiput of the patient, and four straps (145) which are secured to a forehead support (2 straps) and nasal mask frame (2 straps). The straps include hook and loop material, such as Velcro™ on one side. The mask frame and forehead supports include loops through which straps can pass.

In one form of known mask, the cushion and frame are glued together, as shown in FIGS. 2a to 2c. FIG. 2c shows a cross-section 2c-2c through FIG. 2a. The frame (160) includes a rim portion (200) surrounding the rear aperture of the frame. There is a corresponding rim portion (220) on the cushion (180) which fits inside the rim (200) on the frame. The two rims (200, 220) are glued together. A disadvantage with this approach is that the cushion cannot easily be removed for separate cleaning from the frame. Furthermore, there is an increased manufacturing cost since gluing requires assembly time and adhesive.

In one known mask, the Modular mask system (ResMed Limited), the frame and cushion are held, together using a tongue (300) and groove (320), as depicted in FIGS. 3a to 3c. The frame (160) is generally triangular in front view. In use, the front of the frame faces away from the patient and the back of the frame faces towards the patient. The rim portion (350) on the frame (160) includes an outwardly extending flange (340) and engages with a corresponding rim (360) on the cushion (180), such that the rims (350, 360) confront along a locus lying generally in the plane of the patient's face. The frame rim (350) further includes a tongue (300) which protrudes rearwardly from the back of the frame and is received in a corresponding complementary shaped groove (320) formed in rim portion (360) of the cushion (180). In addition, the rim (350) of the frame (160) and the rim (360) of the cushion (180) include aligned slots (380) through which headgear straps (145) can pass. Hence the slots (380) and straps (145) make a contribution to holding the frame (160) and cushion (180) together, in addition to the use of the tongue (300) and groove (320).

In another known mask, a tongue and groove mechanism is used to hold the frame (160) and cushion (180) together, and the tongue (500), which is positioned on the frame (160) has an irregular cross-section as depicted in FIGS. 4a to 4c. The side (520) of the tongue (500) on the interior of the frame (160) is flat. The other side (540) of the tongue (500) has a lateral projection (560) approximately at right angles to the tongue (500). The groove (580) of the cushion (180) has a complimentary shape, including a lateral recess (585) for receiving projection (560). The connection relies on the elasticity of the cushion to retain the cushion in place.

The present invention aims to provide an improved arrangement.

SUMMARY OF THE INVENTION

The present invention provides a respiratory mask assembly for delivering breathable gas to a patient, comprising (i) a substantially rigid mask frame defining a cavity with a rear opening, and a rim portion surrounding said rear opening, said rim portion including a rearwardly projecting tongue, (ii) a flexible mask cushion acting to space the mask frame away from the patient's face, said cushion having a rim portion which includes a groove receiving said projecting tongue of the mask frame, and wherein an outer surface of the cushion forms a rearwardly facing shoulder, and (iii) a clip member passing over the mask cushion, having cushion retaining means engaging behind said shoulder of the cushion and securing means which engages the mask frame so as to retain the mask cushion on the mask frame.

Preferably, the clip's securing means includes at least one securing tab which engages a respective recess in the mask flame, and more preferably on a lateral flange of rim portion of the frame.

Preferably also, the clip is formed as a collar member having a plurality of tabs angularly spaced about the collar member, and the mask frame has a respective plurality of the recesses.

BRIEF DESCRIPTION OF THE DRAWINGS

FIG. 2a shows a perspective view of a form of prior art mask frame and cushion which are glued together FIG. 2b shows a side view of the mask shown in FIG. 2a.

FIG. 2c shows a cross-sectional view of the mask shown in FIG. 2a.

FIG. 3b, shows a side view of the mask shown in FIG. 3a.

FIG. 3c shows a cross-sectional view of the mask shown in FIG. 3a.

FIG. 5b shows a side view of the mask frame shown in FIG. 5a.

FIG. 6e shows a view from the patient (rear) side of the mask cushion shown in FIG. 6a.

FIG. 7a shows a perspective view of a clip suitable for the nasal mask frame of FIGS. 5a and 5b and the nasal mask cushion of FIGS. 6a to 6f.

FIG. 7b shows a view of the clip shown in FIG. 7a.

FIG. 7c shows an enlarged section 7c-7c through the clip in the position indicated in FIG. 7b.

FIG. 7d shows an enlarged section 7d-7d through the clip in a position indicated in FIG. 7b.

FIG. 7e shows a side view of the clip shown in FIG. 7b.

In FIGS. 6a to 6f and 7a to 7e dimensions are shown in millimeters.

FIG. 8a is a rear perspective exploded view illustrating the cushion and frame according to a full face mask embodiment.

FIG. 8b is an assembled view of the cushion and frame of FIG. 8a, along with the clip.

FIG. 9a is a front perspective exploded view illustrating the cushion and frame according to the full face mask embodiment.

FIG. 9b is an assembled view of the cushion and frame, along with the clip.

FIG. 10a is an exploded side view of the cushion and frame according to the full face mask embodiment.

FIG. 10b is an assembled view of the cushion and frame, along with the clip.

FIG. 14a is an exploded front view of the frame and cushion according to the full face mask.

FIG. 14b is an assembled view of the cushion and frame, along with the clip.

DETAILED DESCRIPTION OF THE INVENTION

The method and apparatus for securing a cushion to a mask frame includes a combination of tongue and groove mechanism and a clip in the form of a collar member which passes over and engages both the cushion and the frame.

Figure 5A:
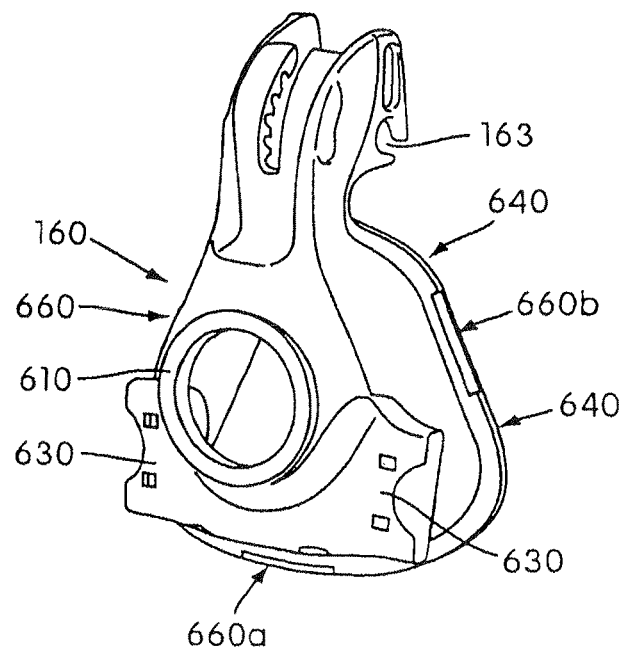
FIG. 5a shows a front perspective view of a nasal mask frame according to an embodiment of the invention.
Figure 5B:
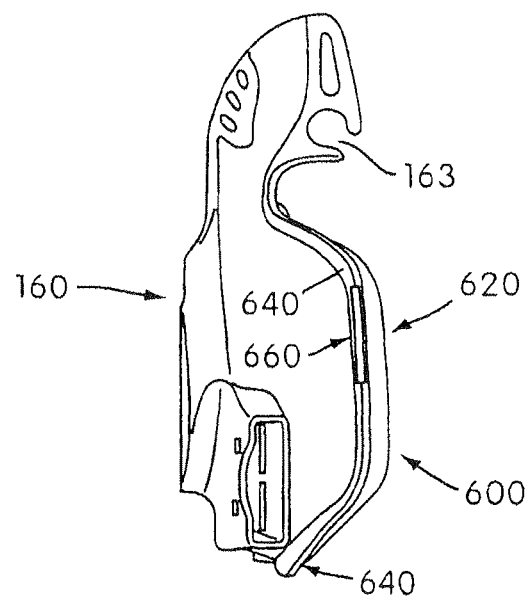
Figure 5C:
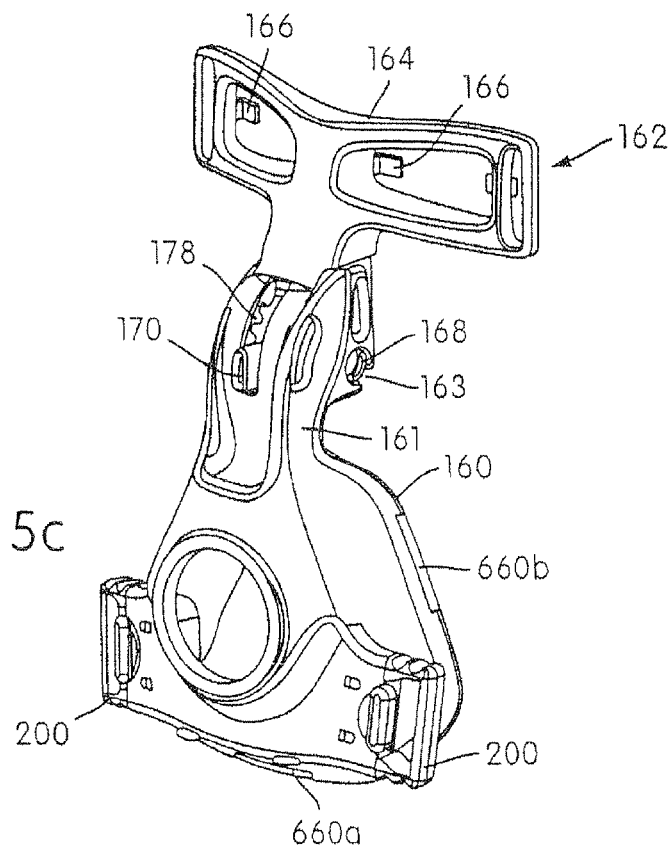
FIG. 5c is a front perspective view of a nasal mask frame and adjustable forehead support according to an embodiment.
Figure 5D:
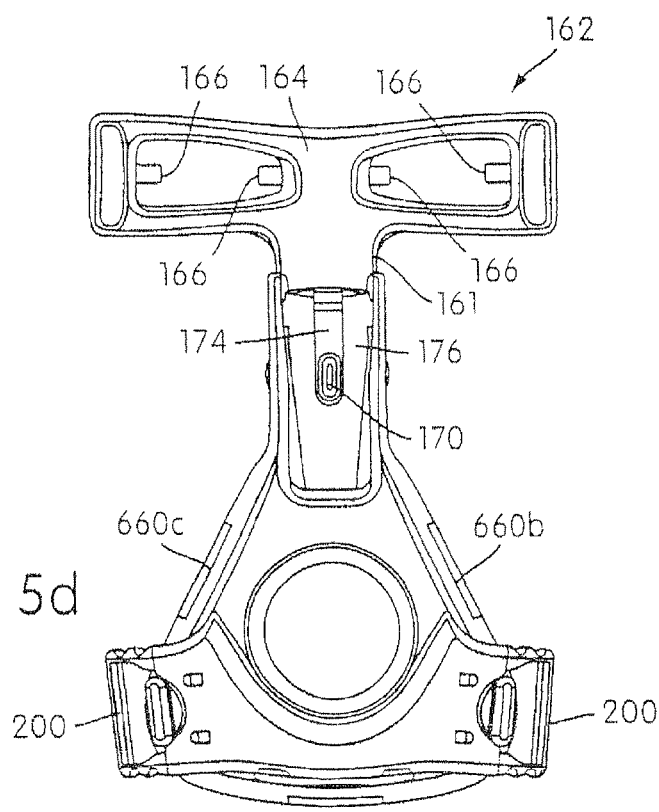
FIG. 5d is a front view of the embodiment of FIG. 5c.
Figure 5E:
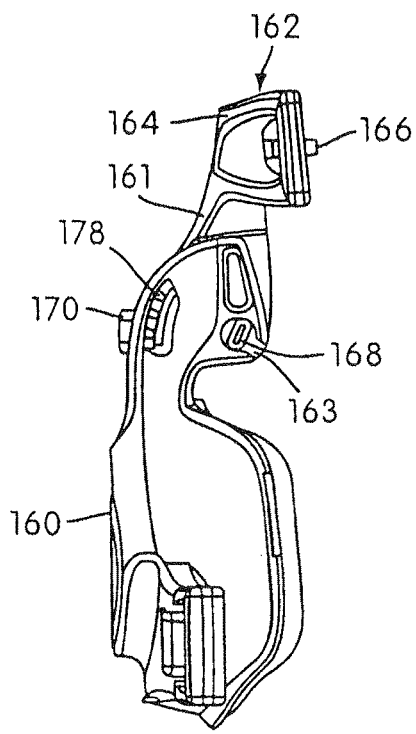
FIG. 5e is a side view of the embodiment of FIG. 5c.

A nasal mask frame including a rim portion according to an embodiment of the invention is shown in FIG. 5a and FIG. 5b. The frame (160) is constructed as a substantially rigid shell of polycarbonate or similar transparent plastics material, and incorporates a gas inlet aperture (610) for connection to a gas delivery conduit (not shown) of a patient gas delivery system.

The frame (160) is generally triangular in front view, covering the patient's nose, and defines a cavity which is open at its rear, the rear opening being surrounded by a rim portion (600) which follows a locus approximating the contours of a patient's face.

On the front surface of the frame, are strap connection points (630) for connection of the mask to patient headgear. Connectors (200) are shown in FIGS. 5c-5f.

As best seen in FIG. 5b, the rim portico (600) of the frame (160) includes a rearwardly projecting tongue (620) and a lateral flange (640). The tongue (620) has an approximately rectangular cross-section. The flange (640) is approximately perpendicular to the tongue (620) and also has an approximately rectangular cross-section. The flange (640) includes three recesses (660) angularly spaced about the rim. Of these, only the bottom recess (660a) and one side recess (660b) are visible in the view of the frame (160) shown in FIG. 5a. The recesses are of an approximately rectangular shape, formed in the front surface of flange (640) adjacent its edge.

FIGS. 5c-5f show additional views of the frame (160). As compared to FIGS. 5a-5b, FIGS. 5c-5f also show an adjustable forehead support (162) connected to the frame (160). The adjustable forehead support (162) includes a bridge portion (164) adapted to locate at least one and preferably two spaced apart pads (not shown) adapted to contact the forehead of the patient. Projection members (166) are formed on the bridge portion (164), and can be used to secure the forehead pads to the bridge portion (164).

The forehead support (162) is coupled to the frame (160) in this example using a pair of small shafts (168) formed on the forehead support (162). The frame (160) includes an extension (161) having a pair of keyed receiving slots (163) to receive the shafts (168). Adjustment is carried out by use of an actuator button (170) coupled in cantilever fashion to the end of a tab (172) formed on the forehead support (162). The actuator button (170) protrudes from the patient side of the extension (161) through a slot (174) (FIG. 5d) formed in the extension (161), thereby exposing the actuator button (170) to the exterior surface (176) of the extension (161), which facilitates access by the patient. The frame (160) is provided with a number of teeth (178), e.g. at least three, to enable the forehead support (162) to be positioned in a corresponding number of positions, so the mask can accommodate patients having a wide scope of facial geometries.

Figure 5F:
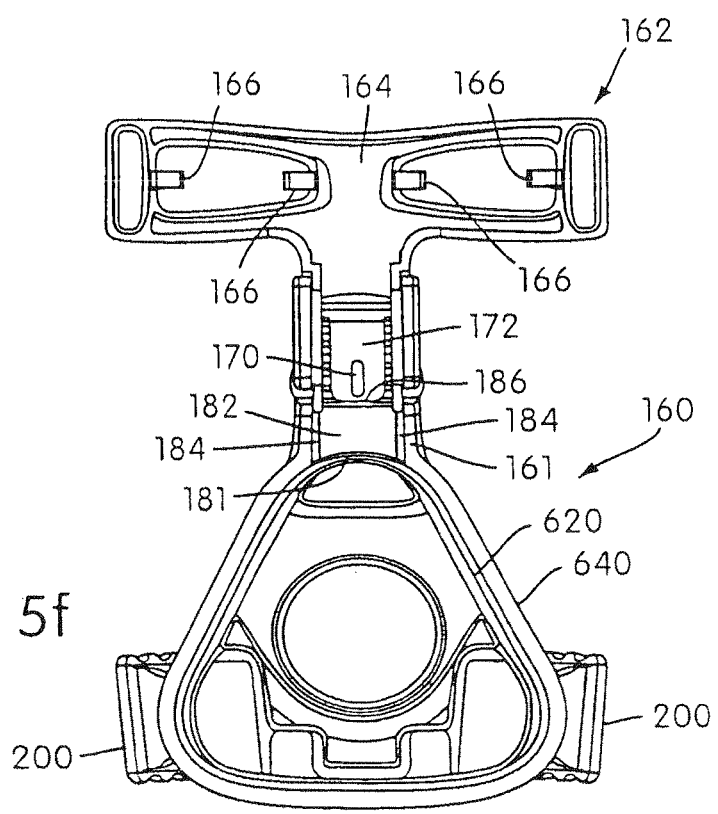
FIG. 5f is a rear view of the embodiment of FIG. 5c.

FIG. 5f shows that the tongue (620) and the flange (640) have a generally triangular shape. An apex (181) of the tongue (620) is provided adjacent to a point where the extension (161) extends upwardly above the main part of the frame (160). A receiving space (182) is defined in a region of the extension (161) just above the apex (181) of the tongue (620). Sidewalls (184) define the side boundaries of the receiving space (182), while the end (186) of the tab (172) defines the upper boundary of the receiving space (182). The purpose of the receiving space (182) will be described below in conjunction with FIGS. 7a-7e.

The thickened rim portion (700) of the cushion has an inwards step (720) in its outer surface, forming a rearwardly facing shoulder.

Figure 6A:
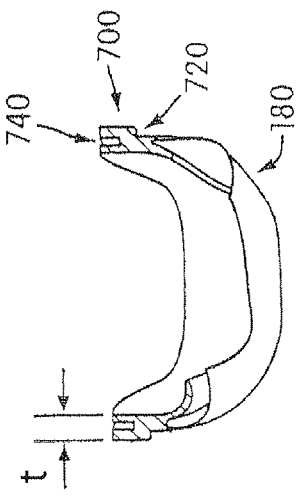
FIG. 6a shows a rear perspective view of a nasal mask cushion suitable for the nasal mask frame of FIGS. 5a and 5b.
Figure 6B:
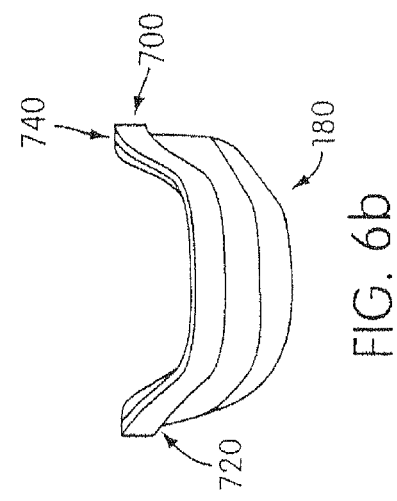
FIG. 6b, shows a side view of the mask cushion shown in FIG. 6e.
Figure 6D:
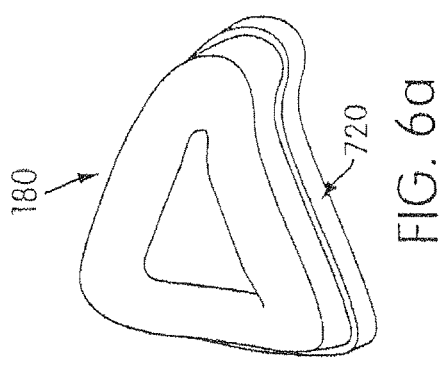
FIG. 6d shows a bottom view of the mask cushion shown in FIG. 6e.
Figure 6C:
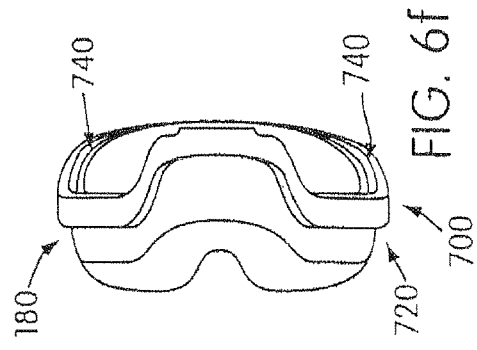
FIG. 6c shows a cross-section through the mask cushion shown in FIG. 6e.
Figure 6E:
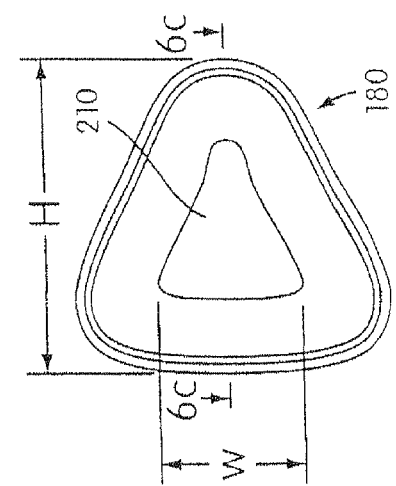
Figure 6F:
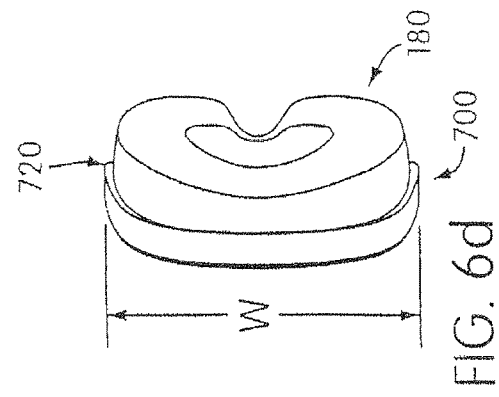
FIG. 6f shows a top view of the mask cushion shown in FIG. 6e.
Figure 11B:
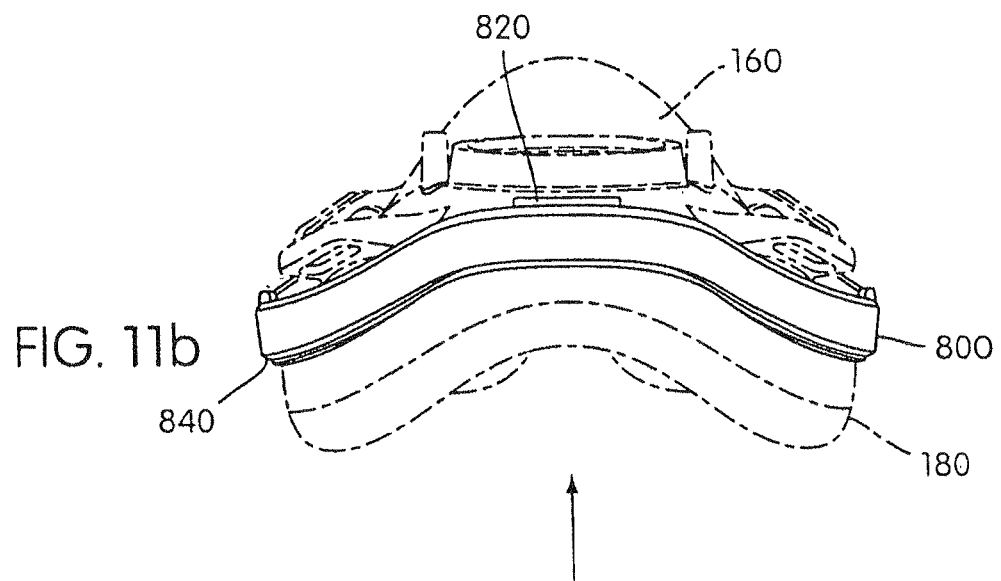
FIG. 11b is an assembled view of the cushion and frame, along with the clip.
Figure 11A:
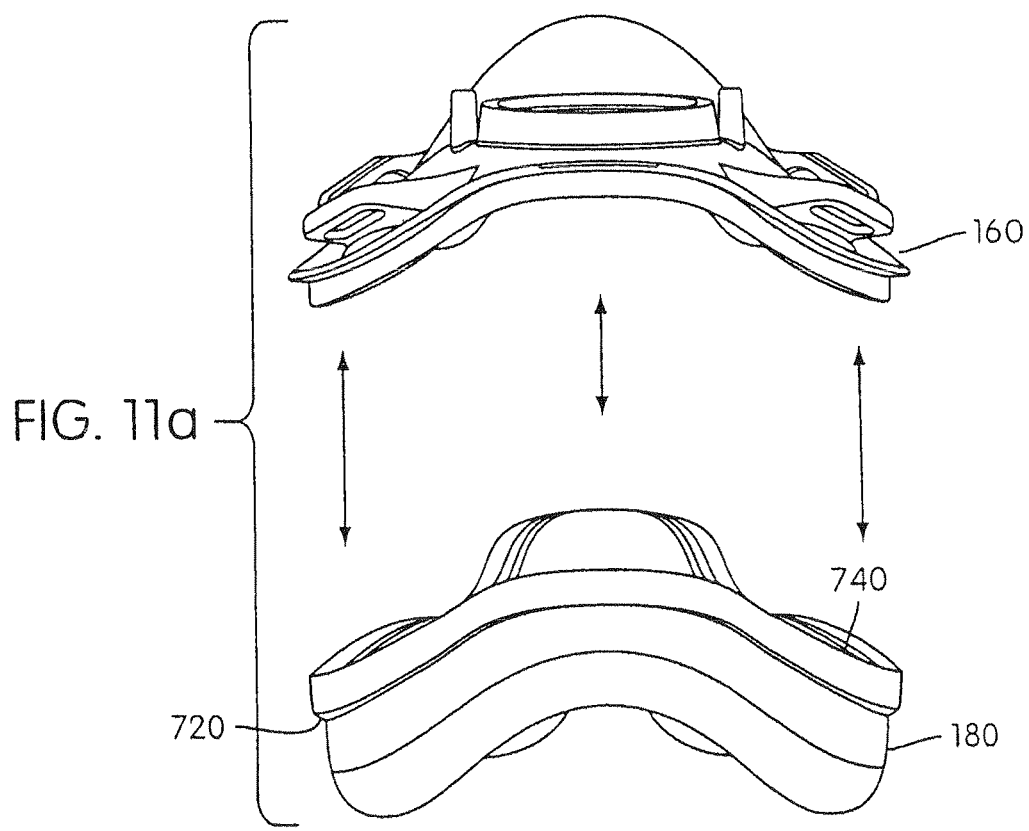
FIG. 11a is an exploded bottom view of the frame and cushion according to the full face mask.
Figure 12B:
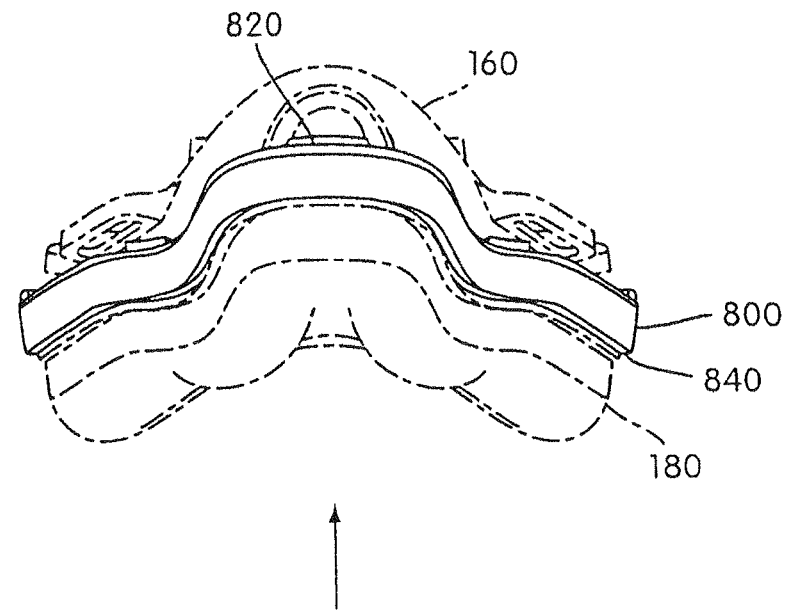
FIG. 12b is an assembled view of the cushion and frame, along with the clip.
Figure 12A:
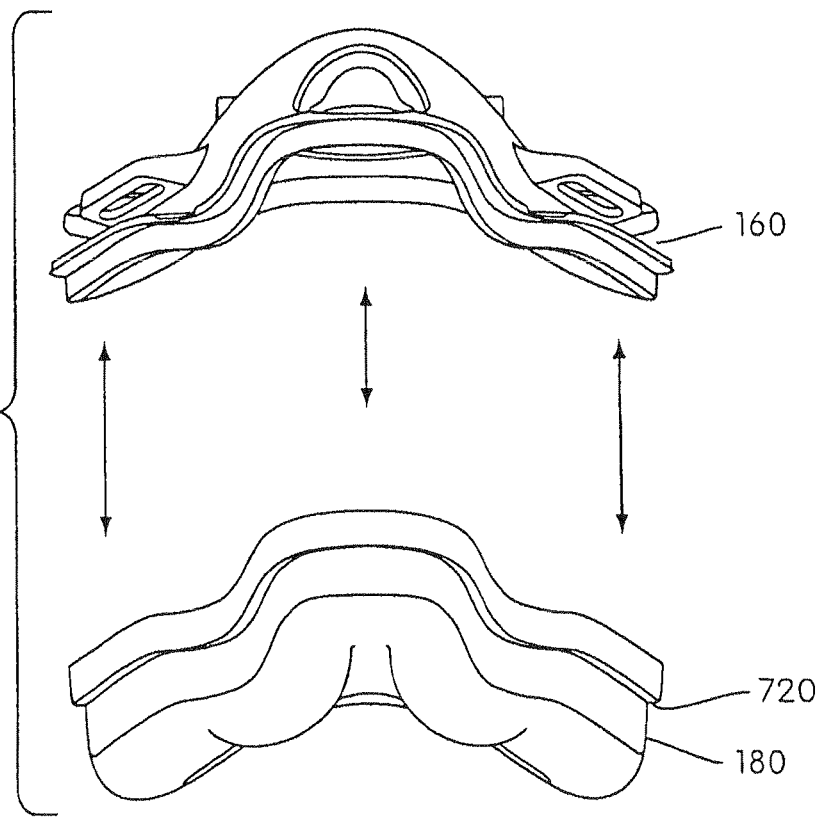
FIG. 12a is an exploded top view of the frame and cushion according to the full face mask.
Figures 13A, 13B:
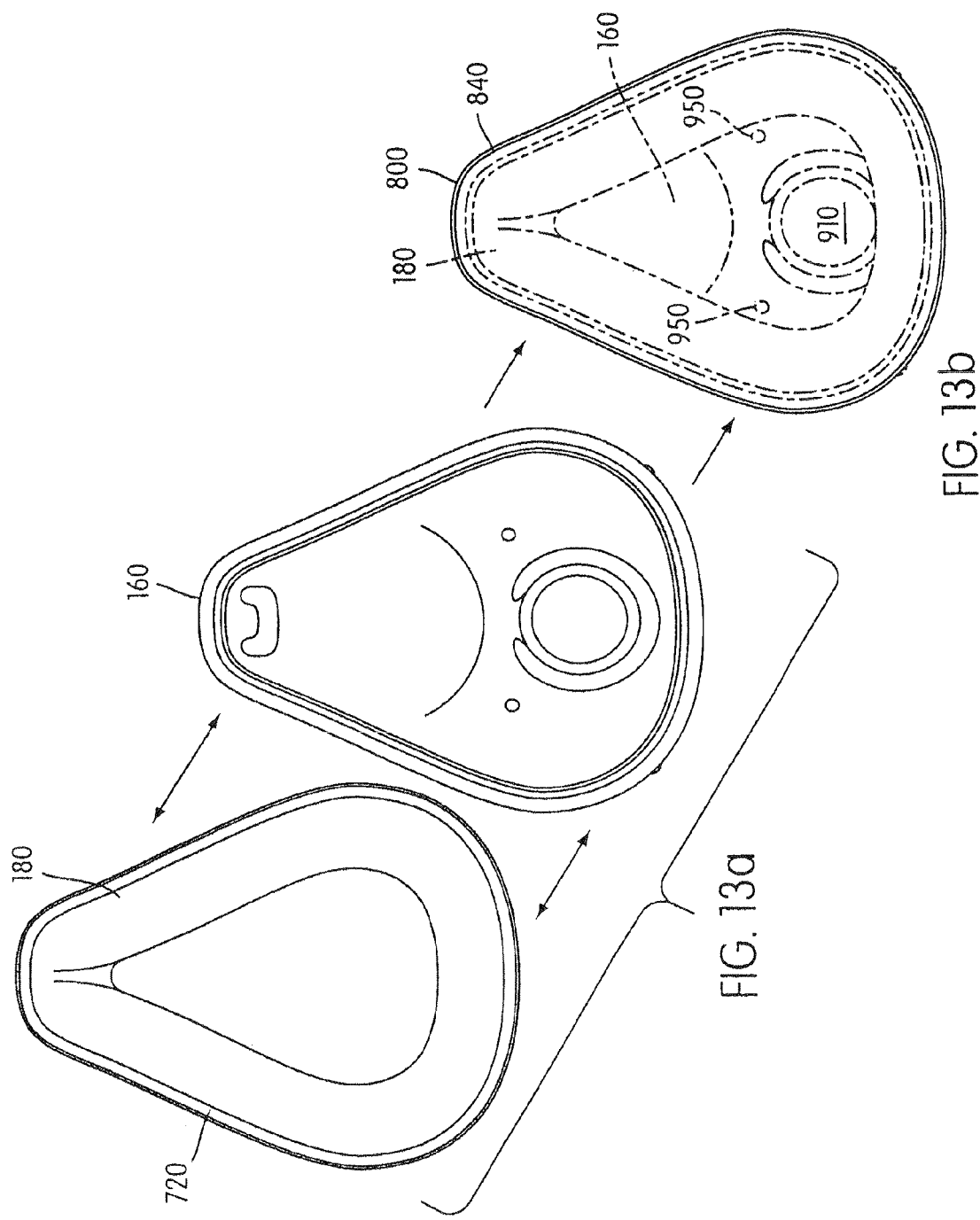
FIG. 13a is an exploded rear view of the frame and cushion according to the full face mask.
FIG. 13b is an assembled view of the cushion and frame, along with the clip.

The cushion is formed of soft material such as silicone, and projects rearwardly of the mask frame so as to space the rigid frame away from the patient's face. The width (W) of the cushion is about 71.2 mm, as shown in FIG. 6d. The width (W) of the aperture 210 is about 31.7 mm. The height (H) is about 72.1 mm. The height of the aperture 210 is about 36.7 mm. The thickness (t) of the lower sidewall is about 6.6 mm, as shown in FIG. 6c.

A clip (800) according to an embodiment of the invention, suitable for a nasal mask, is shown in FIGS. 7a to 7e. The clip is formed as a collar of a complementary shape to the rims of the mask cushion (700) and frame (600) and fits over them. The clip is constructed from polycarbonate or similar material. In the illustrated embodiment the clip (800) includes three securing tabs (820) such that inwards projections on the detents are formed as resilient detents which extend past the outer edge of flange (640) to be retained in recesses (660) on the front of the flange (640). To disengage, for example for cleaning of the mask assembly or replacement of the cushion, the detents may be forced outwardly against their natural resilience to release from the recesses (660) and ride over the outer edge of flange (640). In other embodiments, other numbers of securing tabs may be used.

The rear of the clip has an inwards flange (840) which engages behind the shoulder (720) of the cushion so as to hold the cushion securely in position on the frame when the tabs (820) are engaged on the rim (600) of the frame.

Furthermore, the clip (800) includes a guide projection (802) located at an apex (804) of the clip (800), as shown in FIGS. 7a, 7b and 7e. The projection (802) is positioned diametrically across from the lowermost securing tab (820), as best seen in FIG. 7b. The projection (802) has an arcuate shape that generally matches the curve of the clip (800) at the apex (804) thereof.

As shown in FIG. 7b, the length (l) of each of the securing tabs is about 18.0 mm. The width (w) of the guide projection (802) is about 15.5 mm, and the width (W) of the base of the clip (800) is about 73.83±0.5 mm.

The guide projection (802) helps guide the clip (800) into place when the clip (800) is secured to the frame (160). In this context, the guide projection (802) is not shown as including inwardly facing detents, which distinguish the guide projection (802) from the securing tabs (820), which have inwardly facing detents. In particular, the guide projection (802) is intended to be received within the receiving space (182), which is shown in FIG. 5f. The guide projection (802) has a shape that is complementary to the shape of the apex (181) of the tongue (620) of the frame (160). The width (w) of the guide projection (802) is dimensioned such that it fits between sidewalls (184) of the extension (161).

Figure 15:
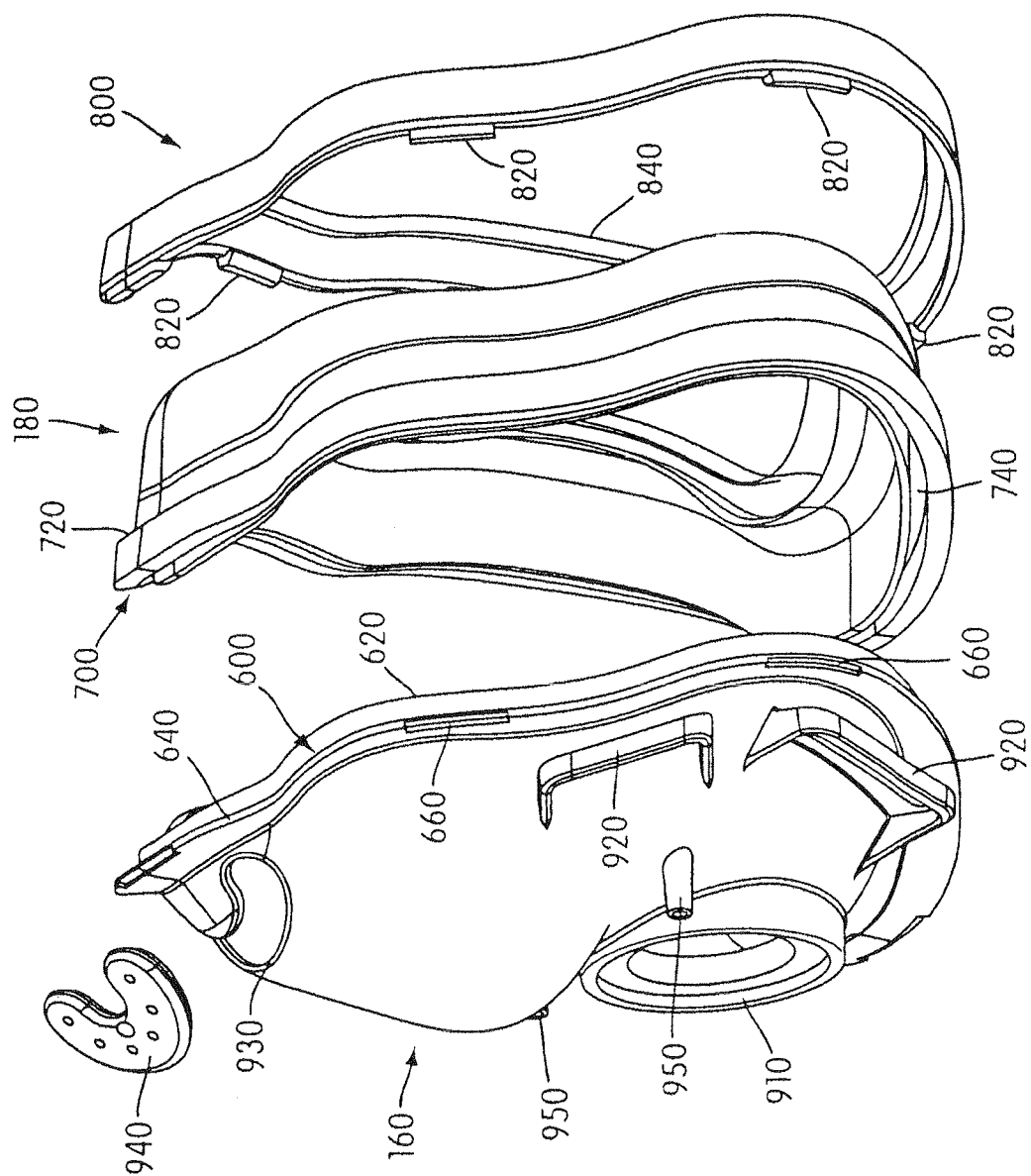
FIG. 15 is an exploded view of an embodiment of the invention as a full-face mask.
Figure 16A:
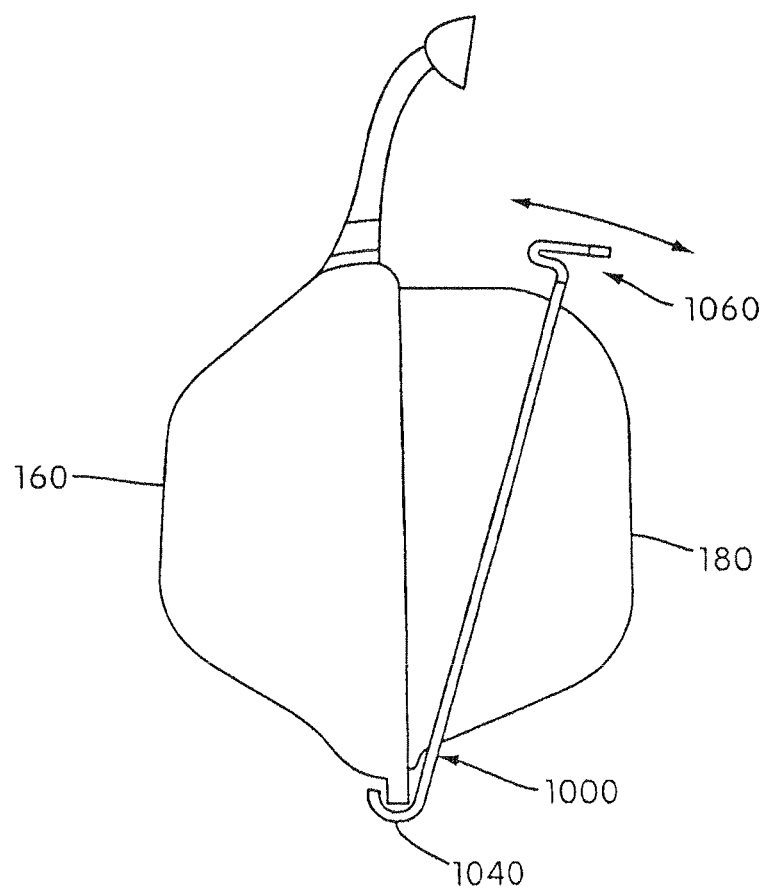
FIG. 16a is a schematic side view of an embodiment employing an alternative clip arrangement.
Figure 16B:
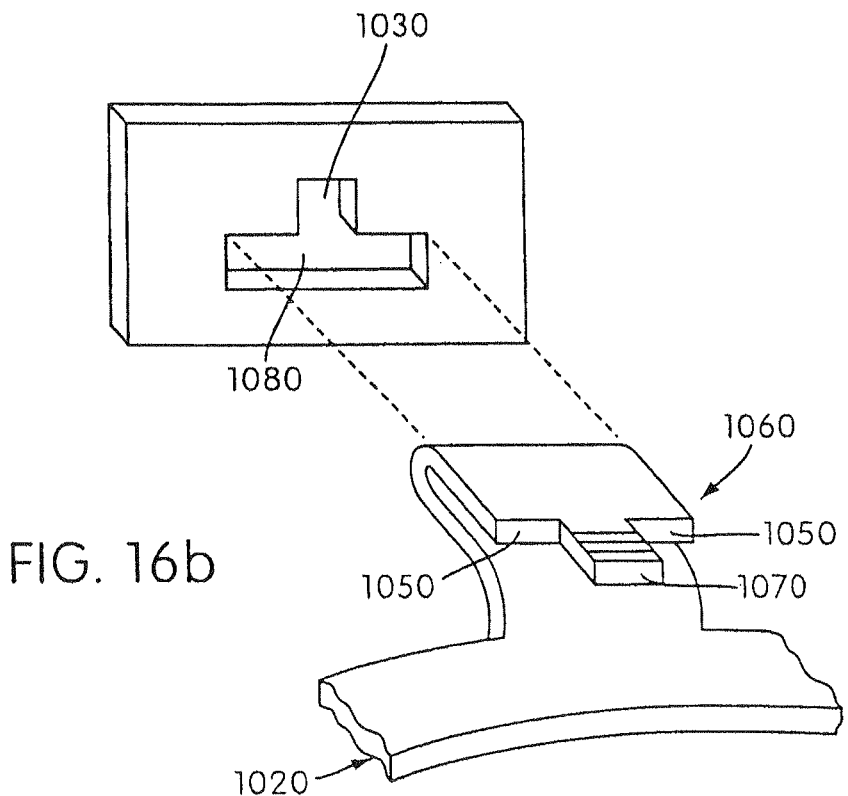
FIG. 16b is a perspective view of engagement of the clip with the mask frame.
Figure 16C:
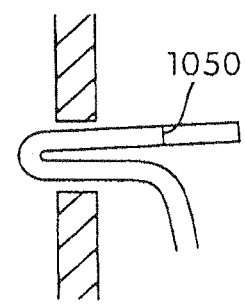
FIGS. 16c and 16d are side views showing clipping of the tab into the slot on the mask frame.
Figure 16D:
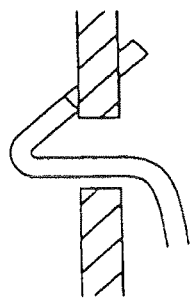

The invention is also suitable for a full-face mask system. FIGS. 8a-15 show several exploded views of a Mirage® full-face mask which includes an embodiment of the invention, including a mask frame (160), cushion (180) and clip (800). While FIGS. 8a, 9a, 10a, 11a, 12a, 13a and 14a show an exploded view of the frame (160) and the cushion (180), FIG. 15 shows an exploded view including the clip (800) as well. FIGS. 8b, 9b, 10b, 11b, 12b, 13b and 14b show the assembled view of the cushion, clip and frame, with the cushion and frame shown in phantom and the clip shown in solid lines. The clip (800) in FIG. 8b can be seen to overlie the cushion (180) since a sidewall (801) of the clip (800) instead of the sidewall (181) of the cushion (180) is visible. In addition, at least one of the securing tabs (820) can be seen. In FIGS. 9a-12a and 14a, recesses (660) can be seen on the frame (160), and FIGS. 9b-12b and 14b show the securing tabs (820) which engage with the recesses (660). FIG. 14b in particular shows that the clip (800) completely surrounds the frame (160), and each of the securing tabs (820) is positioned within respective recesses (660). FIG. 14b also shows that the recesses (660) are slightly larger than the securing tabs (820) in length so as to allow for a small degree of misalignment, to facilitate assembly. The frame is adapted to cover both the mouth and nose region of the patient's face, and includes a gas inlet aperture (910), connection points (920) for headgear straps, an aperture (930) for receiving an air vent (940) (FIG. 15) and ports (950).

The interengagement of the clip (800) and the respective rim portions (600), (700) of the frame (100) and cushion (180) are similar in principle and construction to those described above with reference to FIGS. 5a to 5f and 7a to 7e, except there are six angularly spaced tabs (820) and the respective recesses (660). As in the nasal mask assembly, the rim portion (600) of the frame includes a tongue (620) and a lateral flange (650) with recesses in its front surface adjacent its edge, the rim portion (700) of the cushion having a complementary groove (740) and rear shoulder surface (720), and the clip having a flange (840) and securing tabs (820) generally as described above for the nasal mask assembly.

FIGS. 16a to 16d illustrate an alternative clipping arrangement. The clip (1000) is again formed generally as a collar, with a rear flange (1020) for engaging the shoulder of the cushion as previously described.

At the base of the clip is a securing hook (1040) which hooks over and engages behind the lateral flange of the mask frame (160), allowing the clip to pivot.

At the top of the clip is a resilient detent arrangement (1060), adapted for engagement with an inverted T-shaped slot (1080) on the upper extension of the mask frame (160) as best shown in FIGS. 9*a* to 9*c*.

Figure 1:
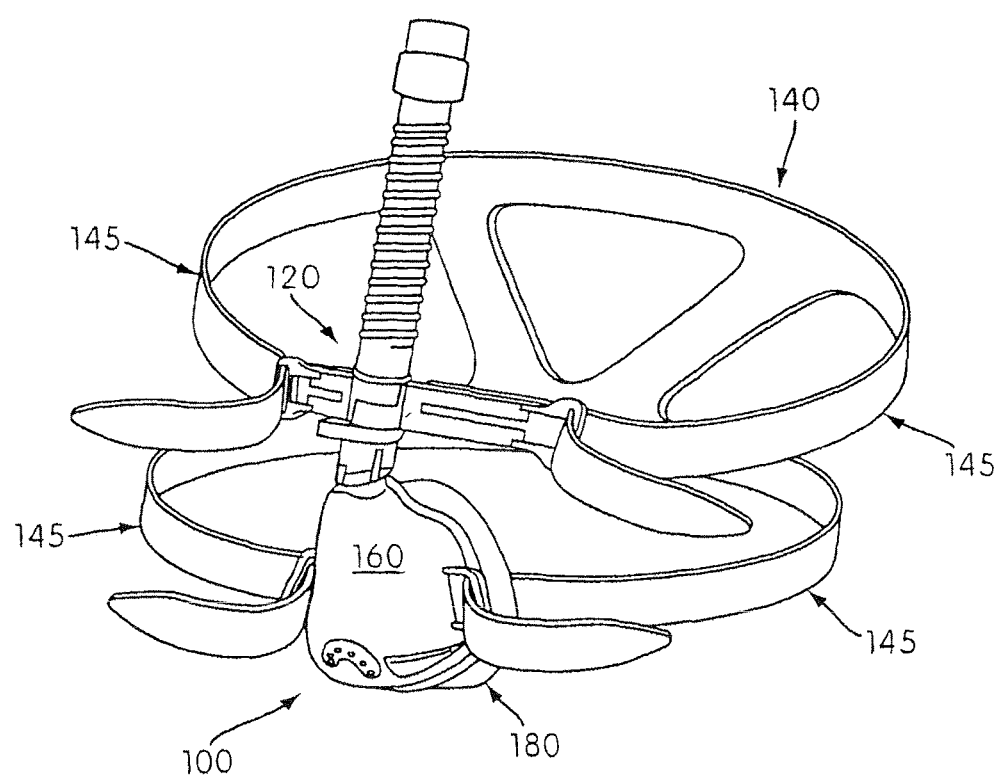
FIG. 1 shows the prior art Mirage® nasal mask system including mask frame, cushion, headgear and forehead support.
Figure 3A:
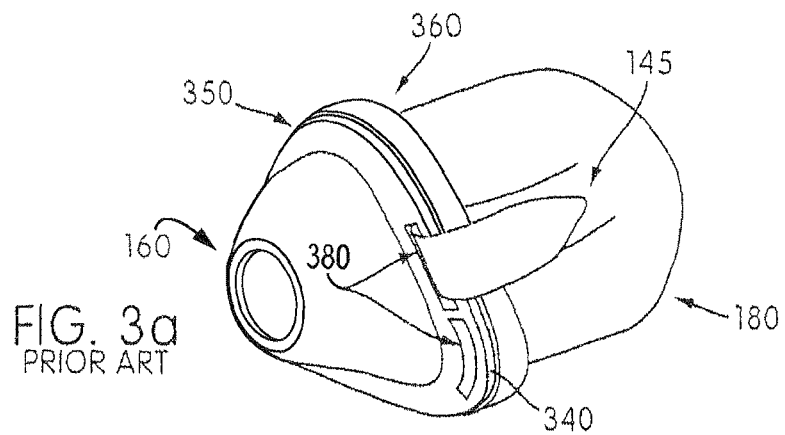
FIG. 3a shows a perspective view of the mask frame and cushion and strap of the prior art ResMed Modular Mask System.
Figure 3B:
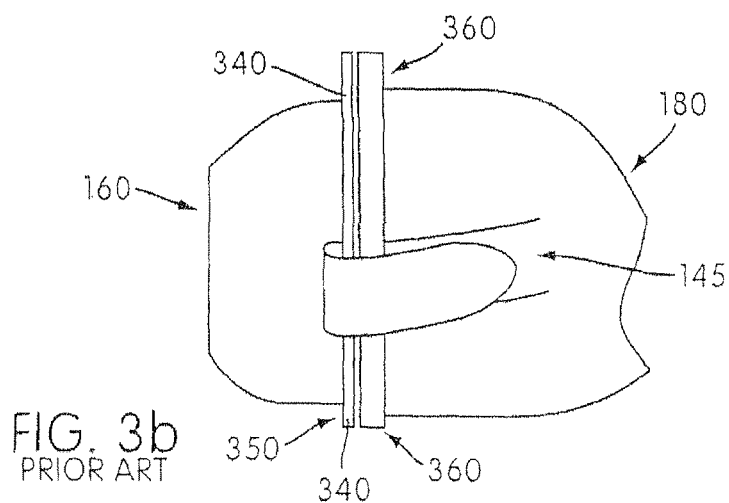
Figure 3C:
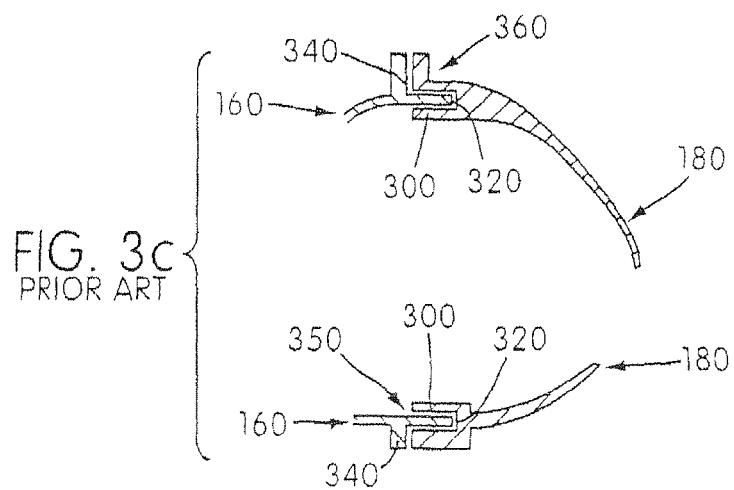
Figure 4A:
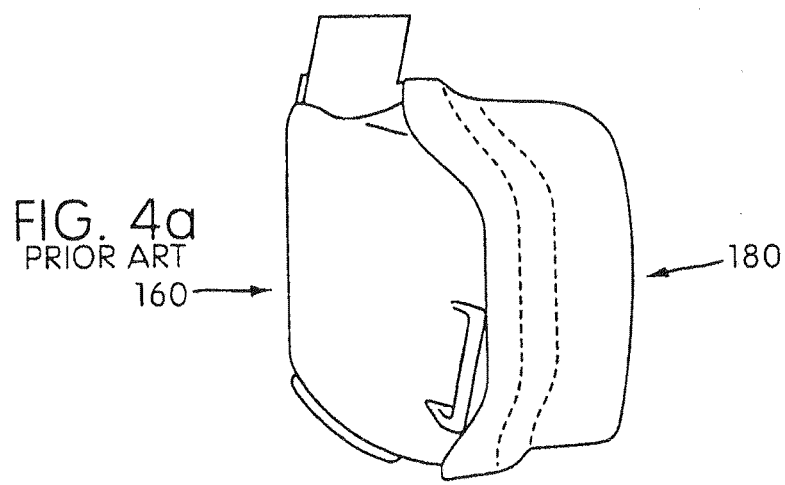
FIG. 4a shows a side view of a prior art mask frame and cushion incorporating a tongue and groove mechanism with an irregular cross-section.
Figure 4B:
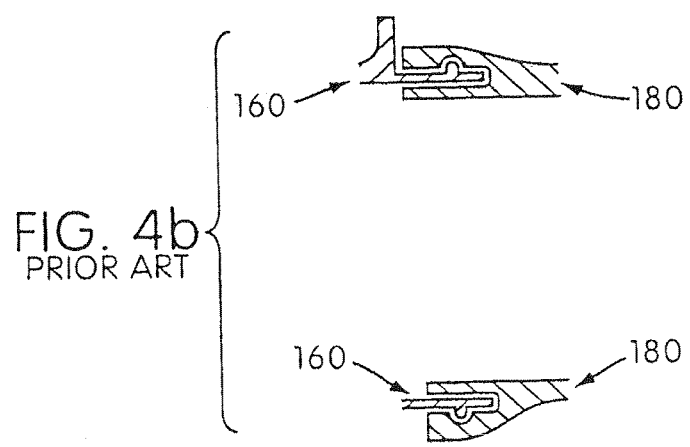
FIG. 4b shows a cross-sectional detail of the mask shown in FIG. 4a where the cushion is secured to the frame.
Figure 4C:
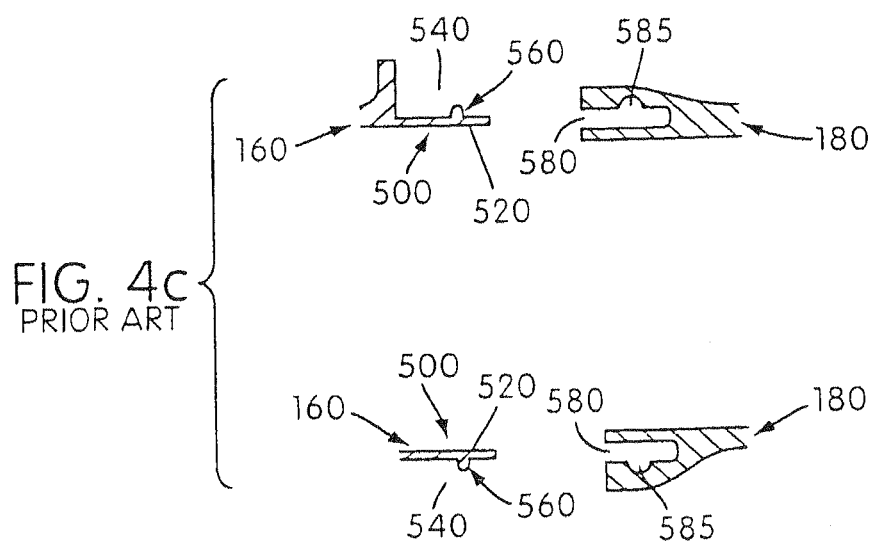
FIG. 4c shows a similar cross-sectional detail of the mask shown in FIG. 4a where the 20 cushion is not secured to the frame.

As shown, the detent is formed as a resilient U-shape with rearwardly facing shoulders (1050) on either side of a narrow tab (1070). In use, the clip is pivoted to force the U-shaped detent through the wide part of the T-slot (1080), until the shoulders (1050) clear the rear surface of the slot. The resilience of the detent then forces tab (1070) into the leg (1030) of the T-slot, to retain the clip in position. To disengage the clip, the tab (1070) is depressed to allow the detent to pass back through the slot In an unillustrated embodiment of the invention, the tongue and groove of the frame and cushion have an irregular cross-section, for example as shown in FIGS. 4*a* to 4*c*.

Although the invention has been described with reference to particular embodiments, it is to be understood that these embodiments are merely illustrative of the application of the principles of the invention. Numerous modifications may be made in the illustrative embodiments of the invention and other arrangements may be devised without departing from the spirit and scope of the invention.

The invention claimed is:

1. A method for assembling a patient interface for treatment of sleep apnea by delivering breathable gas under pressure above ambient to at least one airway of a patient while sleeping, said patient interface including a substantially rigid frame defining a cavity with an opening, a silicone seal to seal with the patient's face, and a substantially rigid clip member, the method comprising:
   engaging the clip member with the silicone seal; and, thereafter,
   moving a resilient portion of the clip member to clip the clip member to the frame such that the clip member retains the seal in contact with the frame and such that the clip member is detachable from the frame.

2. The method of claim 1, further comprising removing the clip member from the frame by resiliently moving a portion of the clip laterally outwards relative to the frame to disengage the clip member from the frame.

3. The method of claim 1, wherein the clip member includes at least one securing tab engageable with the frame.

4. The method of claim 1, wherein said seal is a nasal seal or an oro-nasal seal.

5. The method of claim 1, wherein the frame and the clip member are made of polycarbonate.

6. The method of claim 1, further comprising patient headgear to secure the patient interface to the patient's head.

7. The method of claim 6, wherein the frame is associated with a slotted point of connection on each lateral side thereof to receive the patient headgear.

8. The method of claim 1, wherein the seal and the frame engage one another via a tongue and groove arrangement.

9. The method of claim 1, wherein the frame includes a plurality of first engagement features along a perimeter of the frame and the clip member includes a plurality of second engagement features engageable with the first engagement features.

10. The method of claim 1, wherein the seal and the clip member are separable.

11. The method of claim 1, wherein the seal and the frame seal when engaged, with no locking, while the frame and the clip member lock relative to one another with substantially no sealing.

12. The method of claim 1, wherein the clip member is structured to be anchored at one end of the frame, and pivoted or articulated to connect another end of the frame.

13. The method of claim 1, further comprising an elbow joint provided to the frame and having a swivel tube adapted to connect to a gas delivery conduit.

14. The method of claim 1, wherein the clip member includes at least first and second securing tabs that are resiliently movable in a direction substantially towards or away from one another when attaching and detaching the clip member and the frame.

15. The method of claim 8, wherein the clip member is resiliently movable in a direction that is laterally outwards relative to an outer edge of the groove to attach and detach the clip member and the frame.

16. The method of claim 1, wherein the clip member includes a plurality of securing tabs that extend past and ride over an outer edge of the frame to attach and detach the clip member relative to the frame.

17. The method of claim 1, wherein the clip member includes a plurality of tabs, the tabs being received within recesses formed in the frame, each tab being resiliently movable in a direction that is laterally outwards relative to an outer edge of the frame to attach and detach the clip member from the frame.

18. The method of claim 1, wherein the seal is between the clip member and the frame after resiliently moving a portion of the clip member to detachably clip the clip member to the frame so as to retain the seal on the frame such that a seal is formed between the seal and the frame.

19. A method for assembling a respiratory device for delivering breathable gas to a patient, said respiratory device comprising a frame having a first cooperating interlocking structure; a cushion provided to the frame; and a plastic cushion clip to retain the cushion on the frame, the cushion clip having a second cooperating interlocking structure and being selectively attachable to and detachable from the frame, the method comprising:
   engaging the cushion and the frame;
   interlocking the first cooperating interlocking structure and the second cooperating interlocking structure with one another in a cooperating relationship to secure the cushion clip on the frame, the first cooperating interlocking structure and the second cooperating interlocking structure are provided to at least two sides of the frame and the cushion clip and include a tab-recess arrangement in which a plurality of resiliently movable tabs are engageable within respective recesses in interlocking relation to clip the clip to the frame; and
   securing an elbow joint to the frame, said elbow joint having a swivel tube adapted to connect to a gas delivery conduit.

20. The method of claim 19, wherein the cushion includes an outwardly extending portion received on a rim extending around the periphery of the frame.

21. The method of claim 19, wherein the cushion clip is structured to fit over the cushion and an outer perimeter of the frame.

22. The method of claim 19, wherein the cushion clip is of complementary shape to the frame.

23. The method of claim 19, wherein the frame is associated with a slotted point of connection on each lateral side thereof to receive patient headgear.

24. The method of claim 19, wherein the plurality of resiliently movable tabs are movable in a direction that is laterally outwards relative to an outer edge of the frame to attach and detach the cushion clip and the frame.

25. The method of claim 19, wherein the cushion is between the cushion clip and the frame after interlocking the first cooperating interlocking structure and the second cooperating interlocking structure with one another in the cooperating relationship to secure the cushion the frame such that a seal is formed between the cushion and the frame.

* * * * *